(12) United States Patent
Caligiuri et al.

(10) Patent No.: US 7,915,043 B2
(45) Date of Patent: Mar. 29, 2011

(54) CD34(+) CELLS AND THEIR METHODS OF USE

(75) Inventors: Michael A. Caligiuri, Columbus, OH (US); Aharon G. Freud, Columbus, OH (US); Michael B. Becknell, Westerville, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 11/908,831

(22) PCT Filed: Mar. 20, 2006

(86) PCT No.: PCT/US2006/009974
§ 371 (c)(1),
(2), (4) Date: Sep. 17, 2007

(87) PCT Pub. No.: WO2006/102209
PCT Pub. Date: Sep. 28, 2006

(65) Prior Publication Data
US 2008/0206205 A1 Aug. 28, 2008

Related U.S. Application Data

(60) Provisional application No. 60/662,975, filed on Mar. 18, 2005.

(51) Int. Cl.
*C12N 5/08* (2006.01)

(52) U.S. Cl. .......................... 435/372; 435/375; 435/383

(58) Field of Classification Search .................... None
See application file for complete search history.

(56) References Cited

OTHER PUBLICATIONS

Freud et al., ( Blood, 2004, vol. 104. p. 93.*
Freud et al., ( Immunity, 2005, vol. 22, pp. 295-304.*
Haas et.al Blood, 1995, vol. 85, pp. 1936-1943).*

* cited by examiner

*Primary Examiner* — Michail A Belyavskyi
(74) *Attorney, Agent, or Firm* — Calfee, Halter & Griswold LLP

(57) ABSTRACT

The present invention provides isolated cells that are selectively enriched for hematopoietic progenitor cells that are precursors for natural killer (NK) cells. These cells are both CD34 and CD45RA positive and express C-integrin $\beta_7$, and are referred to as CD34$^{dim}$CD45RA$^{(+)}$C-integrin $\beta_7^{bright}$. The invention provides methods for isolating these cells, for inducing formation of CD56$^{bright}$ NK cells, and for treating diseases associated with immunodeficiency and cancer.

17 Claims, 9 Drawing Sheets

CD34(+) CELLS AND THEIR METHODS OF USE

PRIORITY CLAIM

This application claims priority to U.S. Provisional Patent Application 60/662,975, filed Mar. 18, 2005, which is incorporated herein by reference, in its entirety.

STATEMENT ON FEDERALLY FUNDED RESEARCH

Research leading to this invention was funded, at least in party, by grants CA68458 and CA95426 (MAC) from the National Cancer Institute. The government has certain rights in this invention.

FIELD OF THE INVENTION

The present invention relates to a novel $CD34^{(+)}$ cell line, which can be found in human lymph nodes, and is called $CD34^{dim}CD45RA^{(+)}\beta_7^{bright}$. Methods for isolating the novel cell type from tissue and methods for its use are also provided.

BACKGROUND OF THE INVENTION

Human natural killer (NK) cells are CD3(−)CD14(−)CD56(+) large granular lymphocytes that can kill infected or transformed cells that fail to express normal MHC class I molecules, thereby complementing protection provided by T cells. Similar to other lymphocytes, the total human NK cell population is heterogeneous, with the $CD56^{bright}$ and $CD56^{dim}$ subsets representing two phenotypically and functionally distinct subsets. $CD56^{bright}$ NK cells have few cytotoxic granules and low expression of the low affinity Fc receptor CD16 and killer immunoglobulin-like receptors (KIR), all consistent with poor cytolytic properties, but are capable of potent activation-induced cytokine and chemokine production.

By comparison, $CD56^{dim}$ NK cells have abundant cytolytic granules and high surface density expression of CD16 and KIR for potent antibody-dependent and natural cytolytic function, with little ability to produce immunomodulatory cytokines. Currently, the developmental relationship between the $CD56^{bright}$ and $CD56^{dim}$ human NK subsets is unclear, as is their site(s) of differentiation. While ≧90% of NK cells in peripheral blood are $CD56^{dim}$, >90% of NK cells in lymph nodes are $CD56^{bright}$. A recent study by Munz and colleagues showed that the resident $CD56^{bright}$ NK cells in lymph nodes and tonsils could be induced with interleukin (IL)-2 to adopt functional and phenotypic qualities of peripheral blood $CD56^{dim}$ NK cells, suggesting that $CD56^{bright}$ NK cells may be less mature than $CD56^{dim}$ NK cells in a sequential scheme of human NK development.

A correlate to this hypothesis is that the human NK cell precursor would need to reside in lymph nodes. Similar to other leukocyte populations, human NK cells are ultimately derived from CD34(+) hematopoietic precursor cells (HPC), yet the precise phenotype of the human NK precursor cell is unknown. Culture of purified human bone marrow CD34(+) hematopoietic precursor cells in either IL-2 or IL-15 primarily results in the generation of $CD56^{bright}$ NK cells. Similarly, mouse NK cells can be generated by in vitro culture of immature bone marrow progenitors in IL-2 or IL-15. Both IL-2 and IL-15 signal in part via a common IL-2/IL-15 receptor (R) β chain, and IL-2/IL-15Rβ-deficient mice are severely deficient in mature NK cells. Indeed, the lineage (Lin)(−)IL-2RP(+) population in mouse bone marrow has clearly been identified as the committed mouse NK precursor cell, however, IL-2/IL-15Rβ expression on freshly isolated human CD34(+) hematopoietic precursor cells is below the limits of detection by flow cytometry. Therefore, while the human NK precursor can be defined by its functional ability to differentiate into a $CD56^{bright}$ NK cell in response to IL-2 or IL-15, the precise phenotype of this CD34(+) hematopoietic precursor cell remains elusive.

Previous work by other laboratories has provided invaluable insight into the phenotype of the CD34(+) human NK precursor by associating surface antigen expression with NK precursor function. For example, Miller and colleagues provided early evidence that co-expression of CD7 on CD34(+) hematopoietic precursor cells selectively enriches for NK precursors. In addition, work by the Chen laboratory demonstrated that the co-expression of CD10 on bone marrow CD34(+) hematopoietic precursor cells identified the human common lymphoid progenitor (CLP) that included the NK precursor. Despite these advances, both CD34(+)CD7(−) and CD34(+)CD10(−) hematopoietic precursor cell populations also contain some NK precursors as determined by differentiation into $CD56^{bright}$ NK cells following incubation in IL-2 or IL-15. Thus, the "all-inclusive" human CD34(+) NK precursor cell remained to be identified.

SUMMARY OF THE INVENTION

The present invention provides isolated NK precursor cells that are identified as $CD34^{dim}CD45RA(+)\beta_7^{bright}$. The present invention also provides an isolated population of human cells that comprises greater than 60%, 70%, 80% or 90% cells that are $CD34^{dim}CD45RA(+)\beta_7^{bright}$.

The present invention also provides methods for producing a population of functional hematopoietic precursor cells enriched for NK precursor cells. In one embodiment, the method comprises (a) obtaining a population of hematopoietic precursor cells; (b) selecting CD34+, CD45RA(+) cells from said population of precursor cells; and (c) further selecting cells expressing integrin $\beta_7^{bright}$ on their surfaces.

In some embodiments, the present invention is thus directed to methods for isolating this novel CD34(+) hematopoietic precursor cell that include at least one negative selection step in which cells expressing other marker proteins are separated and removed from the desired cell set. This negative selection step can involve antibodies to, for example, CD3, CD4, CD19, CD36, and glycophorin A.

According to such embodiments, the methods further include a Ficoll-centrifugation step, in which mononuclear cells are separated from other cell types. The methods include a CD34(+)-cell positive selection step in which antibodies to CD34(+) are used. The methods also include a cell-sorting step in which cells that are $CD34^{dim}$, CD45RA(+), and integrin $\beta_7^{bright}$ are separated from other cells.

Also provided by the invention are methods for producing $CD56^{bright}$ NK cells from the $CD34^{dim}CD45RA(+)\beta_7^{bright}$ cells. In one embodiment the natural killer cells are produced in vitro by contacting a hematopoietic cell population having greater than 60%, 70%, 80%, 90% or more cells that are $CD34^{dim}CD45RA(+)\beta_7^{bright}$ with a composition comprising one or both of IL-2 and IL-15. The present invention thus provides methods for providing $CD56^{bright}$ NK cells from a population of hematopoietic precursor cells comprising the steps of (a) obtaining an isolated population of hematopoietic precursor cells that are enriched with cells that are CD34(+), CD45RA(+), and express integrin $\beta_7^{bright}$ on their surfaces; (b) contacting the isolated population of cells with one or both IL-2 and IL-15 in an amount effective to stimulate differentiation of some or all of the cells into CD56$^{bright}$ NK cells.

The present invention also provides methods for treating an individual suffering from immune deficiency, cancer, or other diseases in which NK action is desirable, the methods comprising administering to the individual CD34$^{dim}$CD45RA(+)$\beta_7^{bright}$ cells in an amount effective to establish a population of hematopoietic cells in said subject. The present invention also provides methods for treating an individual suffering from immune deficiency, cancer, or other diseases in which NK action is desirable, the methods comprising administering to the individual CD56$^{bright}$ NK cells produced by the methods disclosed herein in an amount effective to relive the symptoms of the disease from which they are suffering.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, may illustrate embodiments of the invention, and together with the description, serve to explain the principles of the invention.

Figure 9:
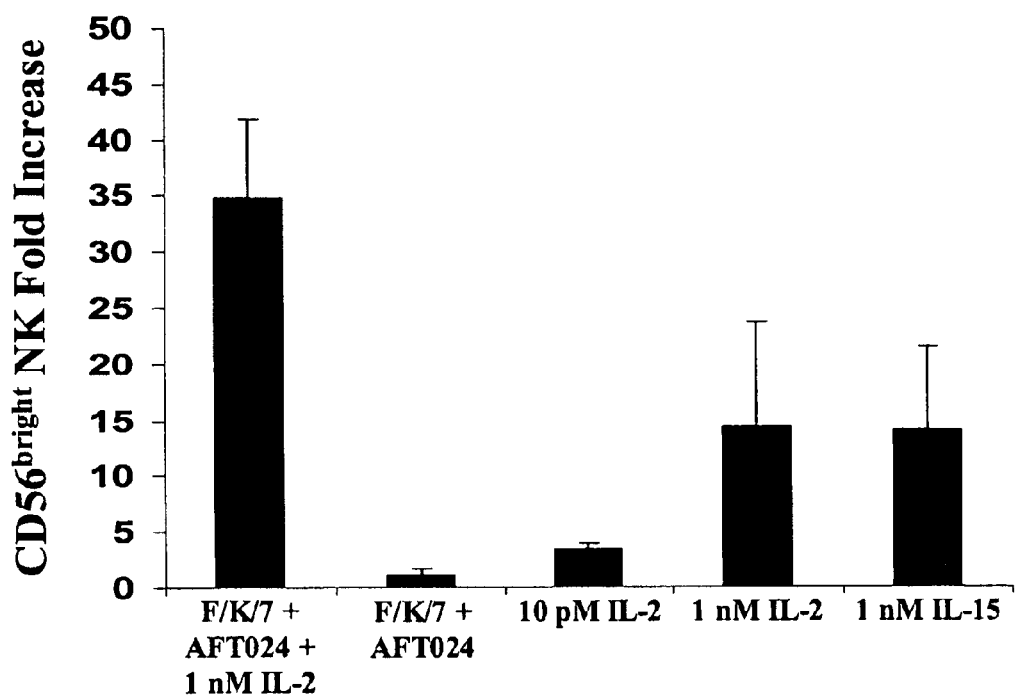

FIG. 9 illustrates cellular yields from peripheral blood CD34$^{dim}$CD45RA(+)$\beta_7^{bright}$ hematopoietic precursor cell differentiation assays. Sorted peripheral blood CD34$^{dim}$CD45RA(+)$\beta_7^{bright}$ cells were cultured for 12 days in 10 pM IL-2, 1 nM IL-2, 1 nM IL-15, or on the AFT024 stromal cell line with 10 ng/ml IL-7 (7), 100 ng/ml c-kit ligand (KL), and 100 ng/ml flt-3 ligand (FL) with or without 1 nM IL-2. Shown are the combined results (±S.D.) from 3 representative donors. The values were obtained by dividing the absolute numbers of CD56$^{bright}$ NK cells enumerated per well at the end of the culture period by the starting number of CD34$^{dim}$CD45RA(+)$\beta_7^{bright}$ cells per well.

DESCRIPTION OF THE EMBODIMENTS

The present invention will now be described by reference to more detailed embodiments, with occasional reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

In accordance with the invention, we have identified a novel subset of CD34$^{dim}$ hematopoietic precursor cells that constitutively express CD45RA and high surface density integrin $\alpha_4\beta_7$ with functional evidence for expression of the heterotrimeric high affinity IL-2R$\alpha\beta\gamma$. This subset of CD34(+) hematopoietic precursor cells, referred to herein as CD34$^{dim}$CD45RA(+)$\beta_7^{bright}$, is selectively and highly enriched within human lymph nodes and resides in the T cell-rich regions along with CD56$^{bright}$ NK cells. The CD34$^{dim}$CD45RA(+)$\beta_7^{bright}$ subset is unique in that differentiation into functional CD56$^{bright}$ NK cells appears to occur exclusively within this CD34(+) hematopoietic precursor cell subset and can occur in the presence of IL-15 or at concentrations of IL-2 that only saturate its high affinity IL-2 receptor. Further, we have shown that activated lymph node T cells can also promote the differentiation of the CD34$^{dim}$CD45RA(+)$\beta_7^{bright}$ NK precursor into a CD56$^{bright}$ NK cell in vitro. The data support a model of human NK development in which a bone marrow-derived CD34$^{dim}$CD45RA(+)$\beta_7^{bright}$ NK cell precursor population selectively resides in lymph nodes where endogenous cytokines can drive its differentiation into CD56$^{bright}$ NK cells in vivo.

Methods for Isolating Cells that are CD34$^{dim}$CD45RA(+)$\beta_7^{bright}$

Peripheral blood, bone marrow or lymph node samples are obtained. Mononuclear cells may be isolated by suitable separation techniques, preferably by density gradient centrifugation over inert, non-ionizable synthetic polymer comprising the crosslinking product of epichlorohydrin and sucrose, available under the trademark FICOLL from Pharmacia, Germany. Samples are treated with antibodies to CD3, CD4, CD19, CD36, and glycophorin A in order to deplete cells expressing these marker proteins during the FICOLL centrifugation step. The mononuclear cells may be further treated in order to enrich the CD34(+)-cells. This can be done by incubating the cells with a monoclonal antibody which is specific for the CD34 antigen. The cells treated with the monoclonal antibody are then loaded onto a magnetic column in order to isolate the CD34(+) cells. The absorbed CD34(+) cells are then removed from the column. It is possible to further enrich the CD34(+) cells by using a fluorescence activated cell sorter which is commercially available from e.g. Becton Dickinson. With the help of the fluorescence activated cell sorter, highly purified cells can be obtained.

Methods for Using CD34$^{dim}$CD45RA$^{(+)}$$\beta_7^{bright}$ Cells to Produce Natural Killer Cells In Vitro The above-isolated CD34$^{dim}$CD45RA$^{(+)}$$\beta_7^{bright}$ cells are resuspended in a suitable medium. Such a medium may constitute, for example, 1640 RPMI with GlutaMAX, 10% heat-inactivated human AB serum, antibiotics, 10 mM HEPES, 100 µm non-essential amino acids, 1 mM sodium pyruvate, and 50 µM 2-BME plus exogenous cytokines. The exogenous cytokines may include one or both of IL-2 and IL-15. In various embodiments, the concentrations of IL-2 or IL-15 can range from about 1, 2, 3, 4, 5, 6, 7, 8, 9, 10, 20, 30, 40, 50, 100, 200, 300, 400, 500, 600, 700, or 800 pmol or higher to about 10, 20, 30, 40, 50, 100, 200, 300, 400, 500, 600, 700, 800, or 900 pmol or higher, or to about 1, 2, 3, 4, 5, 6, 7, 8, 9, or 10 µM. In some embodiments, the concentration of IL-2 can range from 1 pM to 1 nM, or from 1-20 pM, or from 5-15 pM, or can be about 10 pM IL-2. In some embodiments, the concentration of IL-15 can range from 900 pM-10 nM, or from 990 pM-5 nM, or can be about 1 nM IL-15. Half of the culture medium is replaced every 3-4 days. Purified cells may be cultured for 2-4 weeks. At the time of final harvest, total cells/well may be determined on a hemacytometer using trypan blue dye exclusion. The absolute number of mature cells may be calculated by multiplying the average number of total viable cells from triplicate wells by the average percent of cells determined by FACS analyses.

In order to test the function of the in vitro-derived NK cells, cultured cells are then pooled and resuspended in complete medium plus 10/ng IL-12 and 100 ng/ml IL-18 for overnight culture at 37 C. Golgi-plug (BD Biosciences) may be added for a 4-hour incubation and cells are stained for surface CD3, CD14, and CD56 and then permeabilized using the Cytofix/Cytoperm reagent. Cells may be stained with either anti-IF-gamma-FITC monoclonal antibody or isotype control-FITC monoclonal antibody, washed, and then analyzed by FACS. Alternatively, cultured cells may be stimulated with recombinant monokines or $5 \times 10^3$ K562 target cells for 72 hours. Supernatants may then be analyzed by ELISA for cytokine production.

Would we want to discuss potential therapeutic uses here? The original disclosure forms contemplates clinical uses such as adoptive therapy into immune compromised patients and cellular vaccination.

DEFINITIONS SECTION

Examples

Experimental Procedures

Purification of CD34(+) Hematopoietic Precursor Cells from Human Tissue

Figure 8:
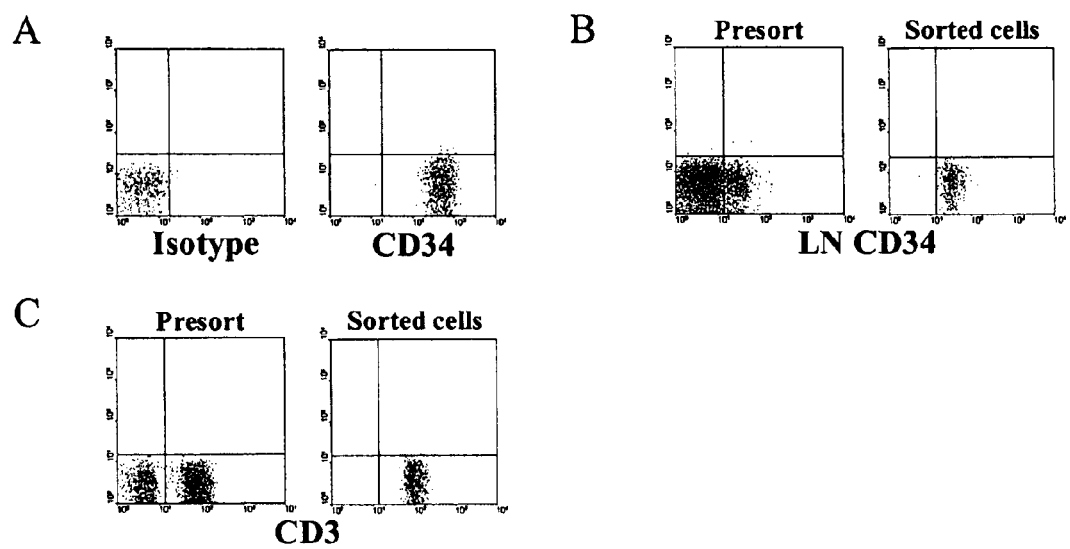
FIG. 8 illustrates representative analyses showing the purity of CD34(+) and CD3(+) cell isolations. (A) After two rounds of positive selection, cells were stained with either an isotype control monoclonal antibody (left) or anti-CD34 monoclonal antibody that does not cross-react with the monoclonal antibodies used for positive selection. (B) Representative analysis showing pre-(left) and post-sort (right) staining for lymph node CD34(+) cells. (C) Representative analysis showing pre-(left) and post-sort (right) staining for peripheral blood and lymph node CD3(+) T cells. In A-C, each of the populations shown are >98% pure.

Fresh human bone marrow was donated or purchased from AllCells, LLC (Berkeley, Calif.) and received within 24 hours of harvest. Peripheral blood leukopaks were obtained from the American Red Cross. Bone marrow or peripheral blood mononuclear cells were enriched by a ficoll-centrifugation step and then total CD34(+) cells were either enriched over 1 magnetic column or purified (>97%, FIG. 8) over 2 magnetic columns using the Miltenyi CD34(+)-enrichment kit (Miltenyi Biotec, Auburn, Calif.). For sorting experiments and phenotypic analyses, total peripheral blood was treated with a rosette cocktail against CD3, CD4, CD19, CD36, and glycophorin A (StemCell Technologies, Vancouver, BC Canada) to deplete cells expressing these markers during the ficoll-centrifugation step. Human lymph nodes were retrieved fresh from surgically discarded tissue from non-cancer patients by the OSU Tissue Procurement Resource and from the National Disease Research Interchange. Lymph node single-cell suspensions were prepared and total CD34(+) cells were enriched as above. Lymph node CD34(+) hematopoietic precursor cells were either stained for flow cytometric analyses or sorted to purity for cell culture.

Flow Cytometry and Cell Sorting

All conjugated and unconjugated experimental and isotype control monoclonal antibodies used in this report were purchased from BD Biosciences except CD16, CD56, CD122 (IL-2Rβ), CD158a, CD158b, NKp30, NKp44, NKp46 (Coulter, Miami Fla.), NG2D (R&D Systems, Minneapolis, Minn.), and AC133 (Miltenyi Biotec, Auburn, Calif.). Non-specific binding was minimized by pre-incubation with whole mouse IgG (direct primary staining) or whole goat IgG (indirect staining) (Sigma, St. Louis, Mo.). Cells were assessed on a FACSCalibur analyzer and analyzed with CellQuest (BD Biosciences) or WinMDI (J. Trotter, Scripps Institute, La Jolla Calif.) software. For culture experiments of purified CD34(+) subsets, cells were sorted on a FACSVantage cell sorter (BD Biosciences) and then sort purities were verified on a FACSCalibur.

NK Cell Development Cultures

IL-2 was provided by Hoffman LaRoche (Nutley, N.J.) and used at the indicated concentrations. Flt3 ligand and IL-15 were provided by Amgen (Thousand Oaks, Calif.), and c-kit ligand and IL-7 were from R&D Systems. Unless otherwise indicated, human NK development cultures were initiated with $2 \times 10^4$ CD34(+) hematopoietic precursor cells in 200 µl complete medium consisting of 1640 RPMI with GlutaMAX, 10% heat-inactivated human AB serum (ICN Biomedicals, Irvine, Calif.), antibiotics, 10 mM HEPES, 100 µM non-essential amino acids, 1 mM sodium pyruvate (all from Invitrogen), and 50 µM 2-βME (Sigma) plus exogenous cytokines. Half the culture medium was replaced every 3-4 days. At the time of final harvest, total cells/well were determined on a hemacytometer using trypan blue dye exclusion. The absolute numbers of mature $CD56^{bright}$ NK cells/well were calculated by multiplying the average numbers of total viable cells from triplicate wells by the average percent of CD3(−)CD14(−)$CD56^{bright}$ NK cells determined by FACS analyses. For CD34(+) hematopoietic precursor cell/T cell co-culture experiments, $0.5-2 \times 10^3$ Peripheral blood CD34(+) hematopoietic precursor cell subsets or total lymph node CD34(+) hematopoietic precursor cells were incubated with $2.5 \times 10^3$ autologous peripheral blood or lymph node CD3(+) T cells (purified via FacsVantage sorting) and stimulated with $5 \times 10^3$ anti-CD3/CD28 beads (Dynal Biotech, Brown Deer, Wis.) in the presence or absence of 10 □g/ml anti-IL-2 or control antibody (R&D Systems). After 7 days of culture, cells were harvested, counted for viability, and stained for flow cytometry.

Functional Analyses of In Vitro-Derived NK Cells

Purified CD34(+) cells were cultured as above for 2-4 weeks. To assess IFN-γ production by intracellular flow cytometry, cultured cells were pooled and then resuspended at $10^6$ cells/ml in complete medium plus 10 ng/ml IL-12 (Genetics Institute, Cambridge, Mass.) and 100 ng/ml IL-18 (BASF, Worcester, Mass.) for overnight culture at 37° C. Golgi-plug (BD Biosciences) was added for a 4-hour incubation, and cells were next stained for surface CD3, CD14, and CD56 and then permeabilized using the Cytofix/Cytoperm reagent (BD Biosciences). Cells were stained with either anti-IFN-7-FITC monoclonal antibody or isotype control-FITC monoclonal antibody, washed, and then analyzed by FACS. Alternatively, cultured cells were stimulated with recombinant monokines or $5 \times 10^3$ K562 target cells for 72 hours, and then supernatants were analyzed by ELISA for cytokine production using Quantikine kits from R&D Systems. CD34(+)-derived $CD56^{bright}$ NK cells were tested for their ability to lyse K562 target cells in a standard chromium-release assay.

Immunohistochemistry and In Situ RT-PCR

Optimal protease digestions of lymph node sections were followed by overnight incubation in RNase free-DNase (10 U per sample, Boehringer Mannheim, Indianapolis, Ind.) and one step RT-PCR using the rTth system and digoxigenin dUTP. The primer sequences for CD34 mRNA detection were: forward 5' accctgtgtctcaacatggca 3'; reverse 5' tctctgat-gcctgaacat 3'. Additional controls included pretreatment with RNase digestion as well as RT-PCR with irrelevant primers (HPV p16 specific primers). Immunohistochemistry staining using an anti-human CD3 monoclonal antibody (Zymed Laboratories Inc., San Francisco, Calif.) was performed.

Statistical Analyses

The paired data were analyzed using an exact Wilcoxon Signed Rank test and the unpaired data an exact Wilcoxon Rank Sum test. S-Plus version 6.0 and SAS version 8.02 were used for the analyses.

Results

Human NK Precursors are Enriched within Peripheral Blood

Figure 1:
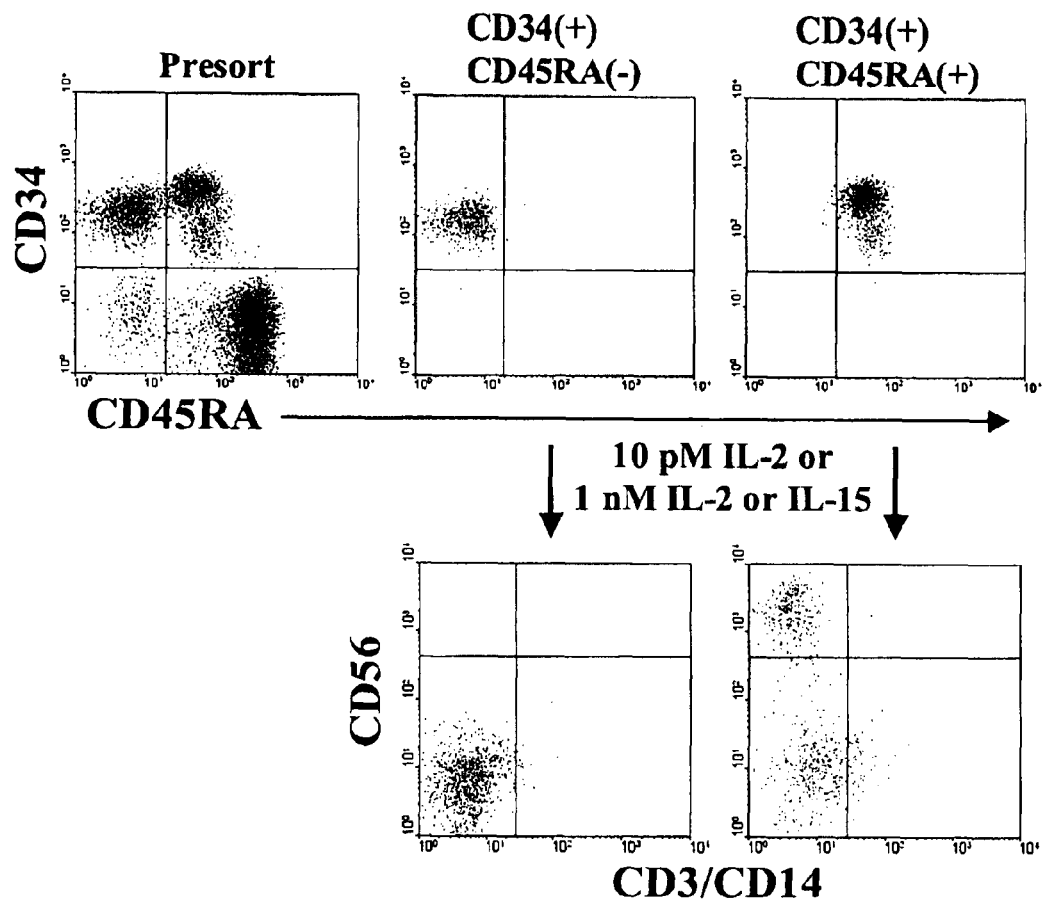
FIG. 1 illustrates co-expression of CD45RA on CD34(+) hematopoietic precursor cells, which identifies the human NK precursor. CD34(+)CD45RA(−) and CD34(+)CD45RA (+) populations from bone marrow (n=3) and peripheral blood (n=7) were sorted and cultured for 2 weeks in 10 pM IL-2, 1 nM IL-2, or 1 nM IL-15. Results shown are representative. Only CD34(+)CD45RA(+) cells differentiate into CD56$^{bright}$ NK cells in IL-2 or IL-15.

The CD56$^{bright}$ NK cell is the only resting lymphocyte population in blood to constitutively express a heterotrimeric high affinity IL-2Rαβγ. To identify its precursor, we first searched for a subset of CD34(+) hematopoietic precursor cells that might also express the high affinity IL-2Rαβγ and differentiate into a CD56$^{bright}$ NK cell via signaling through this receptor. The high affinity IL-2Rαβγ is unique in that it can signal following the binding of very low concentrations (10 pM or 2.3 U/ml) of IL-2, and this binding can be completely abrogated with the anti-IL-2Rα monoclonal antibody. This population was found entirely within the CD45RA(+) subset of CD34(+) hematopoietic precursor cells of both bone marrow and peripheral blood (FIG. 1). We observed identical results in nanomolar concentrations of either IL-15 or IL-2 that utilize the shared IL-2/IL-15Rβγ but not the IL-2Rα (not shown). Importantly, there was a significant difference in the absolute numbers of CD56$^{bright}$ NK cells derived from 2×10$^4$ CD34(+) bone marrow hematopoietic precursor cells (537±340, n=9) versus an equal number of peripheral blood CD34(+) hematopoietic precursor cells (6831±4329, n=5) (P=0.0013), suggesting that peripheral blood contains a much higher percentage of CD34(+) NK precursors than bone marrow (see below).

Figure 2:
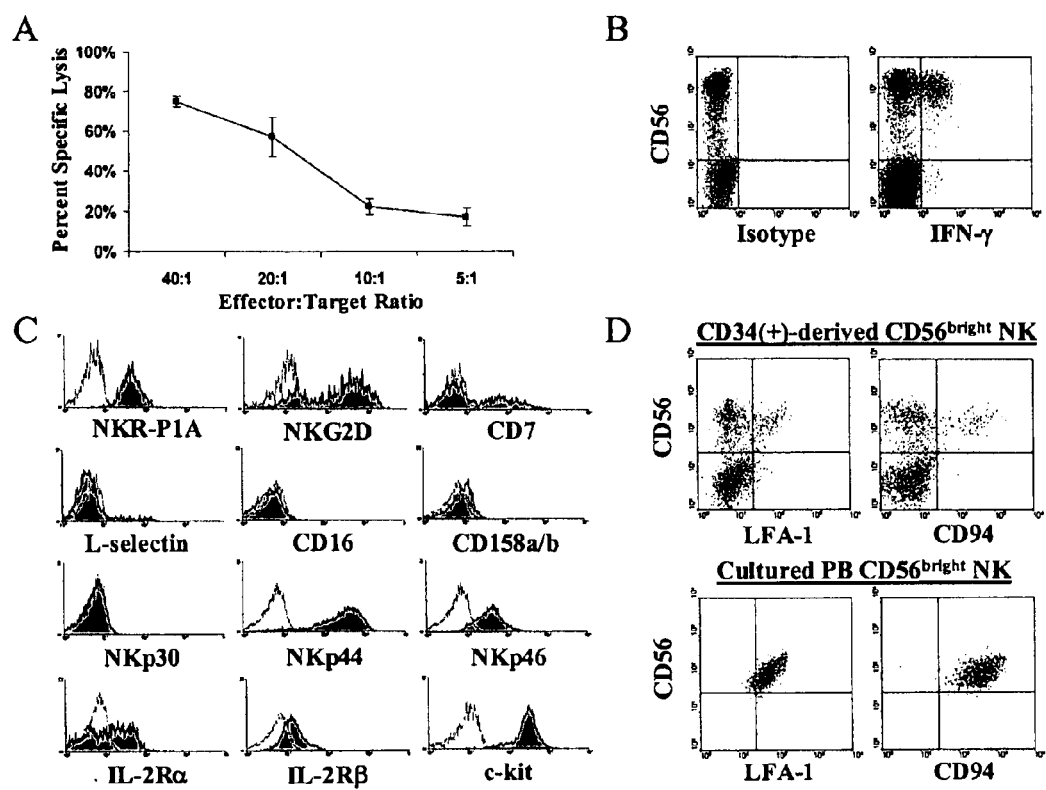
FIG. 2 illustrates functional and phenotypic attributes of CD34(+)-derived CD56$^{bright}$ NK cells. (A) CD34(+)-derived CD56$^{bright}$ NK cells are cytotoxic against K562 target cells at the indicated effector:target cell ratios. Results are representative of 6 experiments. (B) IFN-γ production by CD34(+)-derived CD56$^{bright}$ NK cells. The dot plots were gated on CD3(−)CD14(−) events. (C) Surface expression of CD34(+)-derived CD56$^{bright}$ NK cells. The histograms were gated on CD3(−)CD14(−)CD56$^{bright}$ events; shaded regions represent staining with the specific monoclonal antibodies as indicated, whereas dotted lines (open regions) represent isotype controls. No consistent differences in function or phenotype were observed between CD56$^{bright}$ NK cells derived from CD34(+) cells of bone marrow or peripheral blood origin. (D) Representative phenotypic comparison of CD56$^{bright}$ NK cells derived from CD34(+) hematopoietic precursor cells following a two week culture in IL-2 or IL-15 versus purified mature peripheral blood CD56$^{bright}$ NK cells cultured for two weeks in IL-2 or IL-15. Comparing FIG. 2C and FIG. 7 also shows a difference in NKp44 expression.
Figure 7:
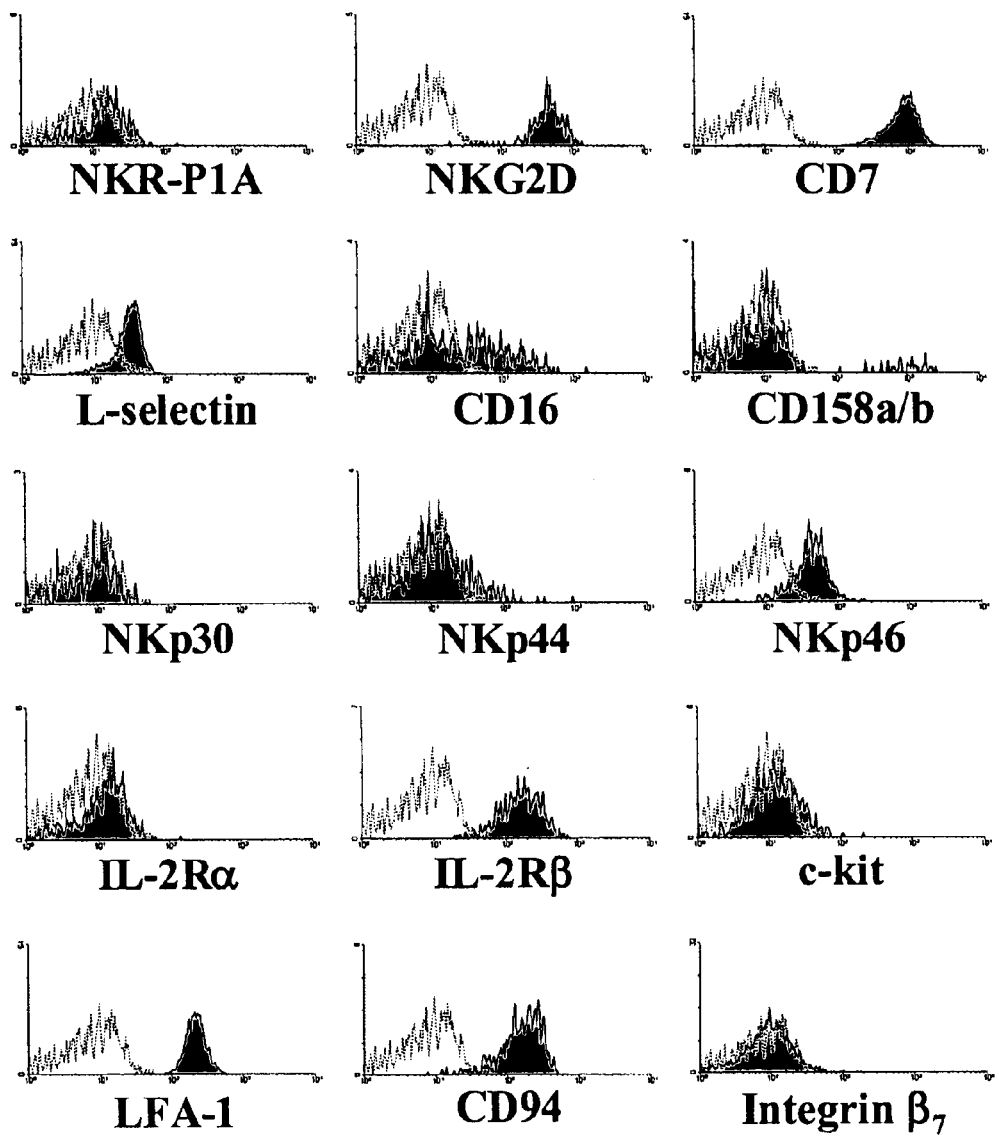
FIG. 7 illustrates representative phenotypic analysis of mature peripheral blood CD56$^{bright}$ NK cells. The histograms are gated on CD3(−)CD14(−)CD56$^{bright}$ events; shaded regions represent staining with the specific monoclonal antibodies as indicated, whereas dotted lines (open regions) represent isotype controls. Compare with CD34(+)-derived CD56$^{bright}$ NK cells (FIGS. 2C and 2D).

Functional and Phenotypic Characterization of the CD34 (+)-Derived CD56$^{bright}$ NK Cells The CD56$^{bright}$ NK cells derived under these conditions from CD34(+) hematopoietic precursor cells were cytotoxic against the NK-sensitive K562 cell line (FIG. 2A) and capable of cytokine production when co-stimulated in recombinant monokines (FIG. 2B and Table 1). Similar to peripheral blood CD56$^{bright}$ NK cells, these cells could not produce cytokines when only co-cultured with K562 targets (not shown). FIGS. 2C and 2D provide a representative phenotype of CD34(+)-derived CD56$^{bright}$ NK cells. We did not observe any consistent phenotypic differences between bone marrow or peripheral blood CD34(+)-derived CD56$^{bright}$ NK cells, but a few distinct differences in phenotype were noted between these cells (FIG. 2C) and mature peripheral blood CD56$^{bright}$ NK cells (FIG. 7). For example, fresh or in vitro cultured mature peripheral blood CD56$^{bright}$ NK cells display uniform expression of CD94 (bright) and leukocyte function-associated antigen-1 (LFA-1), whereas most of the CD34(+)-derived CD56$^{bright}$ NK cells lack these antigens (FIG. 2D). Given these qualitative differences in phenotype, the consistent high purities of our CD34 preparations (FIG. 8), and the very limited growth potential of mature peripheral blood CD56$^{bright}$ NK cells cultured ex vivo, the detection of CD56$^{bright}$ NK cells following prolonged cultures of CD34 (+) hematopoietic precursor cells with IL-2 or IL-15 cannot result from contamination by mature peripheral blood CD56$^{bright}$ NK cells. Rather, these data collectively show that the human NK precursor cell which differentiates to a CD56$^{bright}$ NK cell in the presence of IL-15 or IL-2 is found exclusively within CD34(+)CD45RA(+) hematopoietic precursor cells and is more abundant in peripheral blood than in bone marrow.

TABLE 1

Cytokine production by in vitro-derived CD56$^{bright}$ NK cells

| Donor # | IL-10 (pg/ml) | TNF-β (pg/ml) | TNF-α (pg/ml) | IFN-γ (pg/ml) | GM-CSF (pg/ml) | IL-13 (pg/ml) |
|---|---|---|---|---|---|---|
| 367 | <3.9 | <7.0 | 37.8 | 68,000 | 94.1 | 177.6 |
| 998 | <3.9 | <7.0 | 23.9 | 110,700 | 729.1 | 272.5 |
| 999 | <3.9 | <7.0 | 31.5 | 103,800 | 1,811.5 | 405.8 |

2 × 10$^4$ purified CD34(+) hematopoietic precursor cells were cultured in 10 pM IL-2 for 2 weeks. Subsequently, one-half the medium was replaced with 2× concentrations of stimulatory monokines, the combinations of which were chosen based on optimal cytokine production by peripheral blood CD56$^{bright}$ NK cells that produce measurable amounts of each of these cytokines. For production of IL-10, cultures were treated with 10 ng/ml IL-12 and 100 ng/ml IL-15. For production of TNF-β, GM-CSF, and IL-13, cultures were treated with 100 ng/ml IL-15 and 100 ng/ml IL-18. For production of TNF-α and IFN-γ, cultures were treated with 10 ng/ml IL-12 and 100 ng/ml IL-18. Cultures that received medium alone or 5 × 10$^3$ K562 target cells had undetectable cytokine levels (data not shown).

Refinement of the Phenotype of the CD34(+)CD45RA(+) NK Cell Precursor

Figure 3:
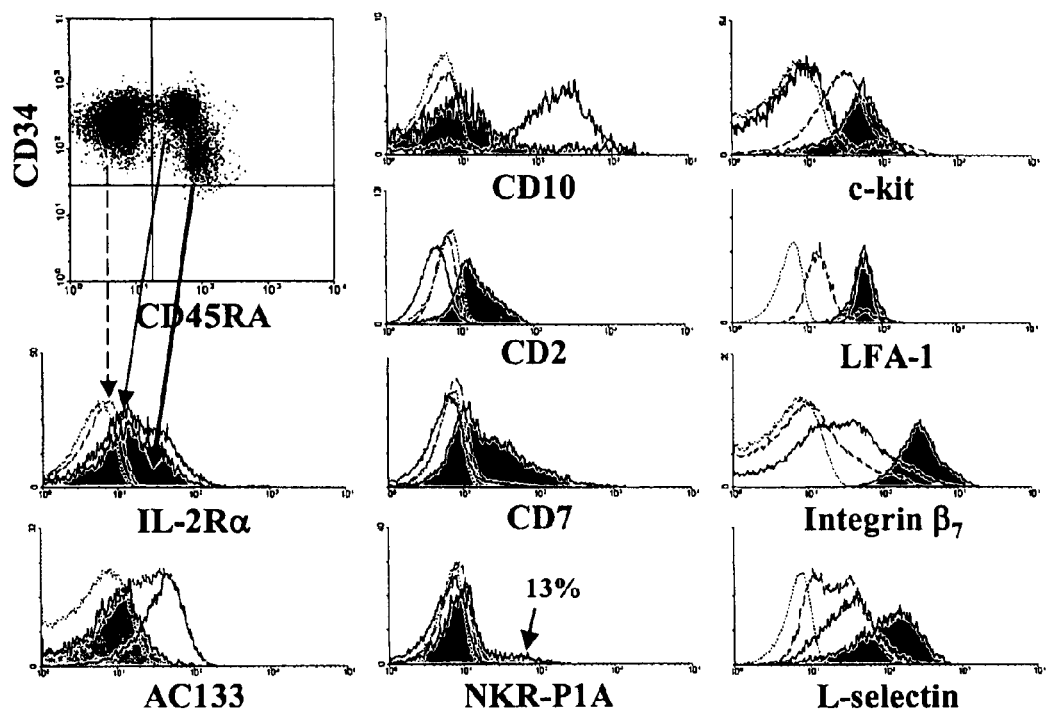
FIG. 3 illustrates a phenotypic analysis of peripheral blood CD34(+) hematopoietic precursor cells subsets. Dotted lines (open regions) in the histograms represent isotype control staining of total peripheral blood CD34(+) cells; shaded regions represent surface expression on CD34$^{dim}$CD45RA (+) cells; solid lines (open regions) represent expression on CD34$^{bright}$CD45RA(+) cells; and dashed lines (open regions) represent expression on CD34(+)CD45RA(−) cells. Prior to staining for flow cytometry, CD19(+) and CD4(+) cells, including pro-B and pro-DC2 hematopoietic precursor cells, were removed. The data shown are representative of 10 donors.

Our statistical analyses of NK precursor frequency in bone marrow and peripheral blood noted above suggested that these CD34(+)CD45(+) NK precursor cells may be trafficking out of the bone marrow to the periphery. We therefore analyzed surface expression of homing and chemokine receptors and cell adhesion molecules (CAMs) on peripheral blood CD34(+) hematopoietic precursor cells. We observed that all peripheral blood CD34(+) cells express similar levels of α$_4$β$_1$ integrin and PEN5 (not shown), whereas CD34(+)CD45RA (+) cells display relatively higher levels of LFA-1 compared to CD34(+)CD45RA(−) hematopoietic precursor cells (FIG. 3). While peripheral blood CD56$^{bright}$ NK cells express CCR7 and CXCR3, we could not detect the expression of either of these chemokine receptors on any peripheral blood CD34(+) subset (not shown). Interestingly, we found that among total peripheral blood CD34(+) cells, a unique CD34$^{dim}$CD45RA(+) subset expresses very high levels of L-selectin and integrinα$_4$β$_7$ (represented by integrin β$_7$ FIG. 3). Of note, these cells are distinct from CD34$^{dim}$CD45RA (+)CD4(+)IL-3Rα$^{bright}$ pro-DC2 cells, which are IL-2Rα(−) c-kit(−)α$_4$β$_7$$^{dim}$ and were depleted from our peripheral blood CD34 preparations with an anti-CD4 monoclonal antibody. The peripheral blood CD34$^{dim}$CD45RA(+) subset we describe here is strikingly reminiscent of mature peripheral blood CD56$^{bright}$ NK cells based on its expression of CD2, CD7, NKR-P1A, and c-kit (shaded histograms in FIG. 3 and FIG. 7). In contrast, the majority of peripheral blood CD34$^{bright}$CD45RA(+) cells (open regions with solid lines in FIG. 3) lack these markers yet express surface CD10, suggesting that this population may be functionally similar to the CD34(+)CD10(+) common lymphoid progenitor previously described in adult bone marrow. In addition, the CD34$^{bright}$CD45RA(+) subset expresses the early stem cell marker, AC133, potentially indicating that this subset is relatively immature compared to the CD34$^{dim}$CD45RA(+) subset that displays no AC133 (FIG. 3).

Figure 4:
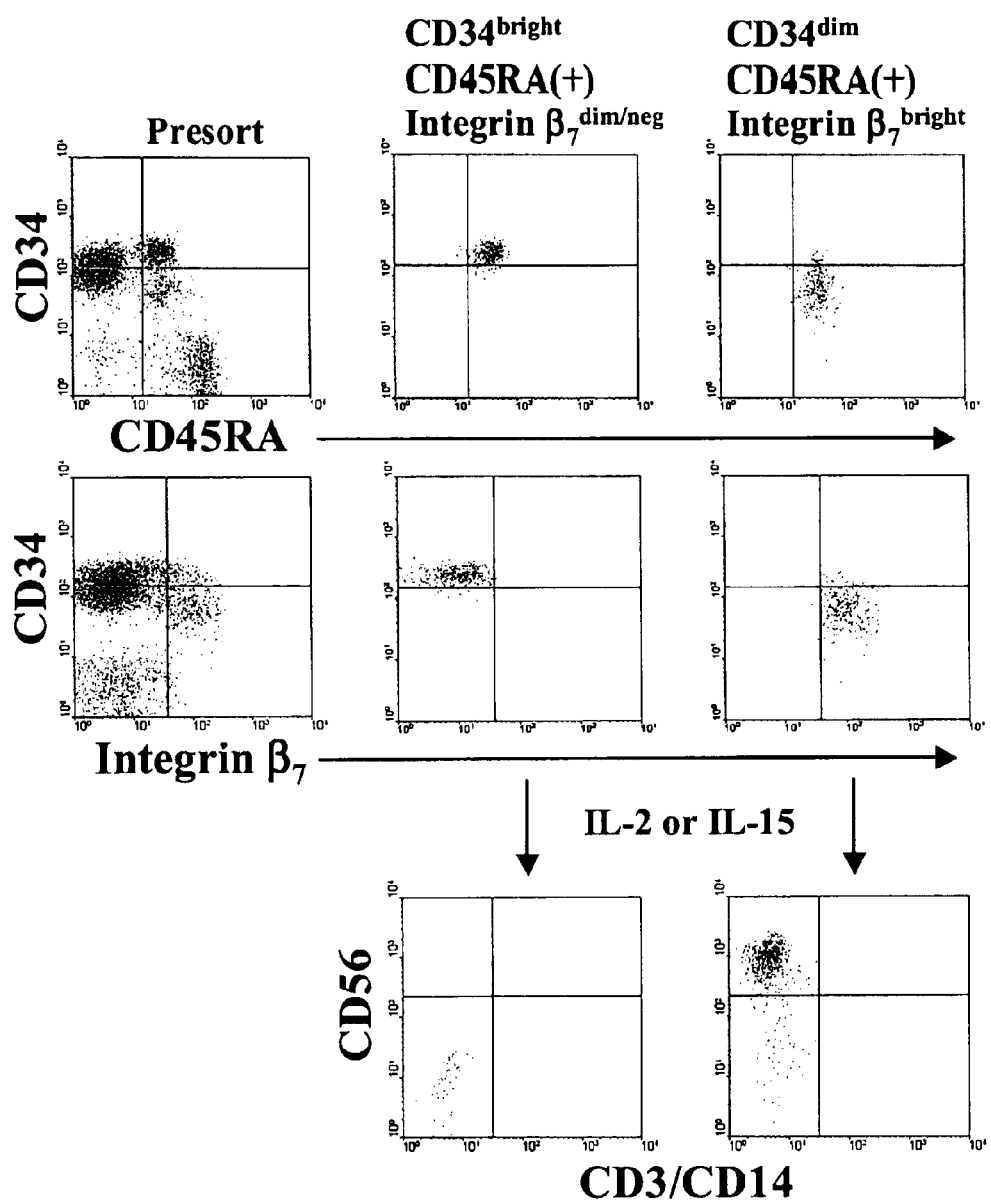
FIG. 4 illustrates that the peripheral blood CD34$^{dim}$CD45RA(+)$\beta_7^{bright}$ subset uniquely differentiates into CD56$^{bright}$ NK cells in IL-2 or IL-15. Peripheral blood CD34$^{bright}$CD45RA(+)$\beta_7^{dim/neg}$ and CD34$^{dim}$CD45RA(+) $\beta_7^{bright}$ cells were sorted and subsequently cultured for 2 weeks in 10 pM IL-2 or 1 nM IL-2 or IL-15 followed by FACS analysis to assess for CD3(−)CD14(−)CD56$^{bright}$ NK cell development. The results are representative of 11 donors.

Subtle overlaps in phenotype between the two peripheral blood CD34(+)CD45RA(+) populations presented an initial challenge to sort these subsets to high purity. For example, not all the CD34$^{dim}$CD45RA(+) cells are CD10(−) and not all the CD34$^{bright}$CD45RA(+) cells are CD7(−) (FIG. 3). Among the surface markers we analyzed, relative bright surface expression of integrin β7 best differentiated the CD34$^{dim}$CD45RA (+) subset not only from other CD34(+) subsets but also from mature CD56$^{bright}$ and CD56$^{dim}$ NK cells, which have absent or low expression of integrin β$_7$, respectively (FIG. 7 and data not shown). Therefore, we used a combination of monoclonal antibodies against CD34, CD45RA, and integrin β$_7$ to purify the two peripheral blood CD34(+)CD45RA(+) subsets and to reduce the potential for mature NK cell contamination in our sorts, a representative of which is shown in FIG. 4. After 2 weeks of culture in 10 pM IL-2 or 1 nM IL-15 or IL-2, we observed that the CD34$^{dim}$CD45RA(+)$\beta_7^{bright}$ subset repeatedly gave rise to CD3(−)CD14(−)CD56$^{bright}$ NK cells (n=11) by FACS with excellent purity (FIG. 4). Generally, we observed only ~1-3-fold expansion when the cells were cultured in 10 pM IL-2, and 15-fold expansion when cultured in 1 nM IL-2 or IL-15 (FIG. 9). However, there was much greater expansion of these cells when cultured on the AFT024 fetal liver stromal cell line in the presence of 1 nM IL-2 and 100 ng/ml of flt3 ligand (FL), 100 ng/ml c-kit ligand (KL), and 10 ng/ml IL-7 (FIG. 9), indicating that these cells are highly proliferative when cultured in the presence of excess cytokines and cellular support. The CD56$^{bright}$ NK cells derived on the AFT024 line displayed the same phenotype as that shown in FIGS. 2C and 2D (not shown). In stark contrast to the results obtained from the CD34$^{dim}$CD45RA(+)$\beta_7^{bright}$ subset, most of the CD34$^{bright}$CD45RA(+)$\beta_7^{dim/neg}$ cells died in culture with only IL-2 or IL-15 (not shown), and none of the live cells had the CD3(−)CD14(−)CD56$^{bright}$ phenotype (FIG. 4). Based on these results and those from FIG. 1, we conclude that the CD56$^{bright}$ NK precursor population is contained exclusively within the CD34$^{dim}$CD45RA(+)$\beta_7^{bright}$ peripheral blood subset.

CD34$^{dim}$CD45RA(+)$\beta_7^{bright}$ Cells Reside in Human Lymph Nodes

In contrast to peripheral blood where ≧90% of NK cells are CD56$^{dim}$, >90% of NK cells in human lymph nodes are CD56$^{bright}$ and are located in the parafollicular T-cell rich regions. One potential model predicts that CD56$^{bright}$ NK cells develop in the bone marrow and traffic to lymph nodes where they participate in the immune response through release of IFN-γ and other cytokines. An alternative model is that bone marrow-derived NK precursors first traffic through peripheral blood to lymph nodes where they can differentiate into CD56$^{bright}$ NK cells in response to endogenous cytokines. Indeed, consistent with the significantly greater number of CD56$^{bright}$ NK cells derived from peripheral blood versus bone marrow CD34(+) hematopoietic precursor cells noted above, <1% of bone marrow CD34(+) hematopoietic precursor cells display the phenotype of the CD34$^{dim}$CD45RA(+)$\beta_7^{bright}$ population shown in FIG. 3 (n=5), compared to ~6% of peripheral blood CD34(+) hematopoietic precursor cells (n=20). These data support the possibility that at least a subset of NK precursors is destined for the periphery. Further, in addition to integrinα$_\square$β$_7$, our data also show that the peripheral blood CD34$^{dim}$CD45RA(+)$\beta_7^{bright}$ subset displays very high surface density expression of LFA-1 and L-selectin (FIG. 3), all three of which can facilitate the extravasation of leukocytes across lymph node high endothelial venules.

Figure 5:
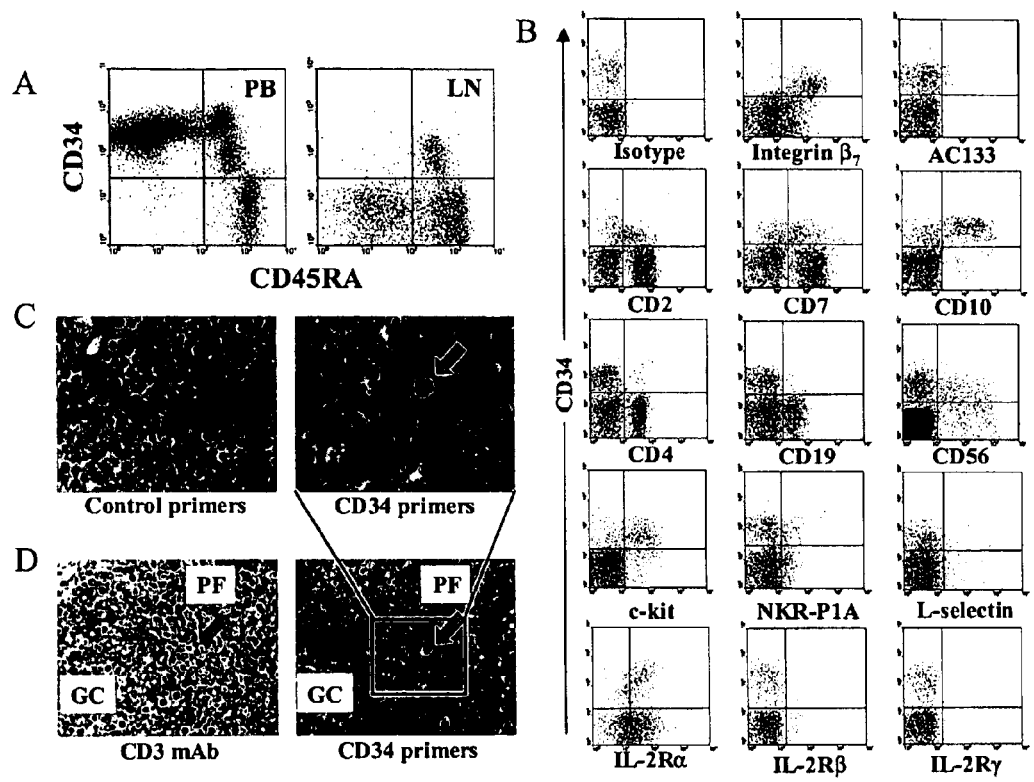
FIG. 5 illustrates discovery of a unique population of CD34 (+) hematopoietic precursor cells in human lymph nodes. (A) Comparative flow cytometric analysis of CD34(+) hematopoietic precursor cell subsets in peripheral blood and lymph nodes following enrichment for CD34(+) cells in each tissue. In contrast to peripheral blood, lymph node CD34(+) cells are almost exclusively CD34$^{dim}$CD45RA(+)$\beta_7^{bright}$. (B) Surface antigen expression of enriched lymph node CD34(+) cells as determined by flow cytometric analysis. The CD34$^{dim}$CD45RA(+)$\beta_7^{bright}$ subset in lymph nodes is strikingly similar to the subset in peripheral blood except for the former's low or absent L-selectin expression (compare with bottom right panel in FIG. 3). (C) RT in situ PCR for CD34 mRNA on human lymph node sections. The power of these images is 1000×. Control primers used in the left panel were specific for the human papilloma virus (HPV) p16 gene. The red arrow in the right panel indicates a representative lymph node CD34(+) cell detected by this method. Note the uniform cytoplasmic signal coming from this cell indicative of cytoplasmic CD34 mRNA. (D) CD34(+) cells reside within the parafollicular T cell-rich regions of lymph nodes. Shown on the right panel is the same lymph node section depicted on the right in C but at a lower power (200×). The red arrow in both images indicates the location of the CD34(+) cell detected by in situ RT-PCR. On the left is a serial section from the same region of the lymph node stained with an anti-CD3 monoclonal antibody. Cells with brown staining are CD3(+). GC, germinal center; PF, parafollicular region.

To test the hypothesis that CD34$^{dim}$CD45RA(+)$\beta_7^{bright}$ cells reside in lymph nodes, phenotypic analyses of CD34(+)-enriched single-cell lymph node suspensions from eight individual donors were performed. In striking contrast to peripheral blood, nearly the entire CD34(+) population discovered within human lymph nodes was CD34$^{dim}$CD45RA(+)$\beta_7^{bright}$ (FIGS. 5A and 5B). Thus, while the CD34$^{dim}$CD45RA(+)$\beta_7^{bright}$ subset represents only ~6% of all peripheral blood CD34(+) hematopoietic precursor cells, this subset represents >95% of all lymph node CD34(+) hematopoietic precursor cells (n=8). This natural and nearly exclusive enrichment for the CD34$^{dim}$CD45RA(+)$\beta_7^{bright}$ subset of CD34(+) hematopoietic precursor cells in lymph nodes eliminates peripheral blood contamination as the source of these cells. Further, peripheral blood CD34$^{dim}$CD45RA(+)$\beta_7^{bright}$ cells express high levels of surface L-selectin while the lymph node CD34$^{dim}$CD45RA(+)$\beta_7^{bright}$ cells had lower or absent expression (compare FIG. 3, bottom right panel to FIG. 5B). This suggests that L-selectin may be involved in the extravasation of peripheral blood CD34$^{dim}$CD45RA(+)$\beta_7^{bright}$ cells into lymph nodes and may subsequently down-regulate upon entrance. As shown in FIG. 5C, we were able to detect CD34 (+) cells within lymph node tissue sections using in situ RT-PCR (note the uniform cytoplasmic staining within the indicated cell). The frequency of CD34(+) cells detected by this method corresponds to an estimate of ~1 CD34(+) cell per 35,000-50,000 total lymph node cells. This is in agreement with the predicted frequency from our flow cytometry data that shows the cell to represent <0.05% of all events without CD34(+) enrichment when using a live forward scatter/side scatter gate (not shown). To our knowledge, this represents the first identification of CD34(+) hematopoietic precursor cells in human lymph nodes. Collectively, these results support the notion that among all peripheral blood CD34(+) hematopoietic precursor cells, it is the CD34$^{dim}$CD45RA(+)$\beta_7^{bright}$ subset that exclusively contains the CD56$^{bright}$ NK precursor and selectively resides in lymph nodes. Formal proof that this cell actually traffics from peripheral blood to lymph nodes will await further study.

T Cell Activation Promotes CD56$^{bright}$ NK Differentiation In Vitro

Figure 6:
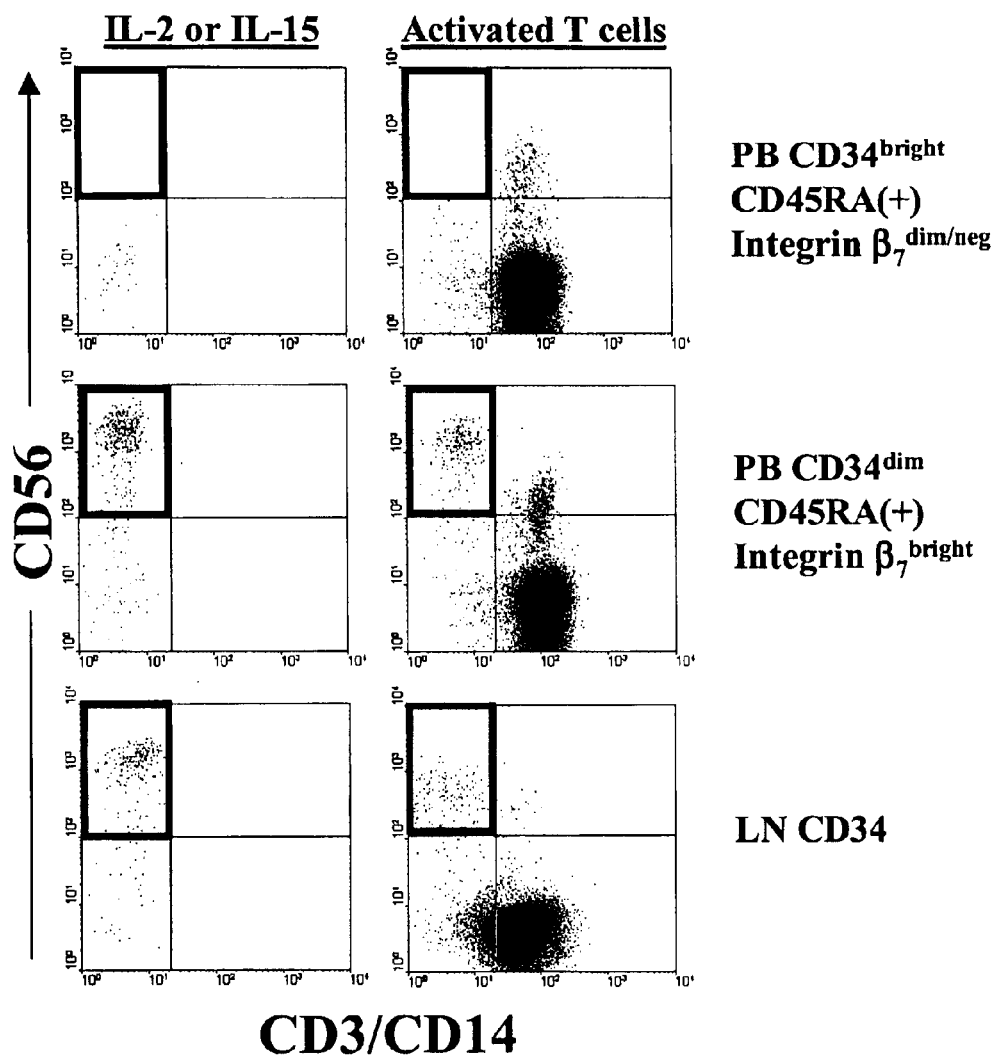
FIG. 6 illustrates how T-cell activation supports CD56$^{bright}$ NK cell differentiation from CD34(+) hematopoietic precursor cells in vitro. Peripheral blood CD34$^{bright}$CD45RA(+) $\beta_7^{dim/neg}$ and CD34$^{dim}$CD45RA(+)$\beta_7^{bright}$ subsets (n=6) or total lymph node CD34(+) hematopoietic precursor cells [>95% CD34$^{dim}$CD45RA(+)$\beta_7^{bright}$] (n=3) were cultured for 7 days in exogenous IL-2 or IL-15 (left column) or co-cultured for 7 days with autologous peripheral blood or lymph node CD3(+) T cells activated via CD3/CD28 stimulation (right column). The CD3(−)CD14(−)CD56$^{bright}$ NK cells derived from these cultures are seen in the upper left quadrant of each histogram. In data not shown, culture of sorted lymph node CD3(+) T cells stimulated with anti-CD3/CD28 beads did not produce any CD56$^{bright}$ NK cells without co-culture of the CD34(+) hematopoietic precursor cells.

Immunohistochemistry staining on serial lymph node sections with an anti-CD3 monoclonal antibody revealed that the CD34(+) hematopoietic precursor cells we observed by in situ RT-PCR (FIG. 5C) were located within T cell rich regions of lymph node sections (FIG. 5D), where CD56$^{bright}$ NK cells also reside. To recapitulate what might occur in vivo during T cell activation, lymph node CD34(+) hematopoietic precursor cells were co-cultured with autologous lymph node CD3 (+) T cells in the presence of CD3/CD28 stimulation. As shown in FIG. 6, we observed CD3(−)CD14(−)CD56$^{bright}$ NK cell development after only 7 days under these conditions, along with a >10-fold increase in activated T cell numbers (not shown). We similarly cultured purified peripheral blood CD34$^{bright}$CD45RA(+)$\beta_7^{dim/neg}$ and CD34$^{dim}$CD45RA(+)$\beta_7^{bright}$ subsets with autologous peripheral blood CD3(+) T cells and observed that similar to the results obtained by 7-day culture in exogenous IL-2 or IL-15, only CD34$^{dim}$CD45RA(+)$\beta_7^{bright}$ cells gave rise to NK cells in the presence of CD3/CD28 stimulated T cells (FIG. 6). The addition of an anti-IL-2 monoclonal antibody to these co-cultures resulted in variable (average 25%, n=9) reduction in CD56$^{bright}$ NK cell development, likely due to the contribution of other endogenous factors (e.g., IL-7, IL-15, IL-21, KL) that might directly or indirectly contribute to this process. Thus, activated lymph node T cells, in close proximity to lymph node CD34$^{dim}$CD45RA(+)$\beta_7^{bright}$ hematopoietic precursor cells, can induce human CD56$^{bright}$ NK cell differentiation without the addition of exogenous cytokines.

Other embodiments of the invention will be apparent to those skilled in the art from consideration of the specification and practice of the invention disclosed herein. It is intended that the specification and examples be considered as exemplary only, with a true scope and spirit of the invention being indicated by the appended claims.

What is claimed is:
1. A method of isolating CD34$^{dim}$CD45RA$^{(+)}$ integrinβ$_7^{bright}$ cells from a biological sample comprising the steps of:
  separating cells expressing at least one first marker protein by using an antibody to the at least one first marker protein;
  isolating mononuclear cells using Ficoll-centrifugation;

isolating CD34(+)-cell positive cells using at least one antibody to CD34(+); and sorting cells in a cell sorter using at least one second marker protein.

2. The method of claim 1, wherein said first marker protein is chosen from CD3, CD4, CD19, CD36, and glycophorin A.

3. The method of claim 1, wherein said second marker protein is chosen from CD34, CD45RA, and integrin $\beta_7$.

4. The method of claim 1, wherein said second marker protein is integrin $\beta_7$.

5. The method of claim 1, wherein the biological sample is obtained from lymph nodes.

6. The method of claim 4, wherein the isolated cells are selected using cytoadhesion.

7. The method of claim 4, wherein the isolated cells are selected using immunomagnetic separation.

8. The method of claim 6 wherein said cytoadhesion uses binding to galactose.

9. The method of claim 8 wherein said cytoadhesion uses binding to N-acetyl galactosamine.

10. The method of claim 9, wherein said N-acetyl galactosamine cytoadhesion is affinity chromatography.

11. The method of claim 9, wherein the N-acetyl galactosamine is conjugated to BSA.

12. The method of claim 4, wherein the isolated cells are purified by equilibrium density centrifugation.

13. The method of claim 1, further comprising fractionating said purified population of hematopoietic precursor cells by fluorescence activated flow cytometry, velocity sedimentation or counter flow centrifugal elutriation.

14. Isolated NK precursor cells that are CD34(+), constitutively express CD45RA and high surface density integrin $\alpha_4\beta_7$.

15. The isolated NK precursor cells according to claim 14 that express heterotrimeric high affinity IL-2R$\alpha\beta\gamma$.

16. A method for producing a population of functional hematopoietic precursor cells enriched for NK precursor cells, comprising:
(a) obtaining a population of hematopoietic precursor cells;
(b) selecting CD34+, CD45RA(+) cells from said population of precursor cells; and
(c) further selecting cells expressing integrin $\beta_7^{bright}$ on their surfaces.

17. A method for isolating CD34(+) hematopoietic precursor cells, comprising
(i) at least one negative selection step in which cells expressing one or more marker proteins selected from the group of CD3, CD4, CD19, CD36, and glycophorin A are separated and removed from the desired cell set;
(ii) a Ficoll-centrifugation step in which mononuclear cells are separated from other cell types;
(iii) a CD34(+)-cell positive selection step in which antibodies to CD34(+) are used to select CD34(+) cells; and
(iv) a cell-sorting step in which cells that are CD34$^{dim}$, CD45RA(+), and integrin$\beta_7^{bright}$ are separated from other cells.

* * * * *

UNITED STATES PATENT AND TRADEMARK OFFICE
CERTIFICATE OF CORRECTION

PATENT NO. : 7,915,043 B2
APPLICATION NO. : 11/908831
DATED : March 29, 2011
INVENTOR(S) : Michael A. Caligiuri, Aharon G. Freud and Michael B. Becknell It is certified that error appears in the above-identified patent and that said Letters Patent is hereby corrected as shown below:

In the Specification

Column 1, Line 13-16, please update the Statement on Federally Funded Research as shown:
This invention was made with government support under grant numbers CA068458 and CA095426 awarded by the National Institutes of Health. The government has certain rights in the invention.

Signed and Sealed this
Twenty-eighth Day of July, 2020

Andrei Iancu
*Director of the United States Patent and Trademark Office*